United States Patent [19]

Park et al.

[11] Patent Number: 5,279,610
[45] Date of Patent: Jan. 18, 1994

[54] OROESOPHAGEAL, INSTRUMENT INTRODUCER ASSEMBLY AND METHOD OF USE

[75] Inventors: Sang C. Park, Pittsburgh, Pa.; Edwin E. Macatangay, Bloomington, Ind.

[73] Assignee: Cook Incorporated, Bloomington, Ind.

[21] Appl. No.: 973,153

[22] Filed: Nov. 6, 1992

[51] Int. Cl.$^5$ .......................................... A61M 25/01
[52] U.S. Cl. ................... 606/108; 606/191; 604/164; 604/264; 604/280; 128/200.26; 128/207.15
[58] Field of Search .................. 606/108, 191; 604/93, 604/96, 158, 164, 171, 264, 170, 280, 270; 128/207.14, 207.15, 200.26

[56] References Cited

U.S. PATENT DOCUMENTS

| 3,543,751 | 12/1970 | Sheffer | 604/96 |
| 4,327,720 | 5/1982 | Bronson et al. | 128/207.15 |
| 4,834,702 | 5/1989 | Rollo | 604/170 |
| 4,865,586 | 9/1989 | Hedberg | 604/93 |
| 4,960,122 | 10/1990 | Mizus | 128/207.14 |
| 5,052,386 | 10/1991 | Fischer, Jr. | 128/207.15 |

FOREIGN PATENT DOCUMENTS

| 107779 | 5/1984 | European Pat. Off. | 606/108 |
| 19285 | 11/1901 | United Kingdom | 604/280 |
| 91/12837 | 9/1991 | World Int. Prop. O. | 604/170 |

OTHER PUBLICATIONS

Marcon, Norman E., MD, FRCPC, "Overtubes and foreign bodies," *Can J Gastroenterol*, vol. 4, No. 9, Dec. 1990, pp. 599-602.

Norfleet, Robert G., MD, FACP, and Skerven, Greg, "Large-Bore Tube for Both Lavage and Passage of Endoscopes," *SGA Journal*, vol. 3, 1980, pp. 18-19.

*Primary Examiner*—Tamara L. Graysay
*Attorney, Agent, or Firm*—Richard J. Godlewski

[57] ABSTRACT

An oroesophageal introducer assembly for atraumatically introducing a relatively large instrument such as an echotransducer positioned on the distal end of a gastroscope for performing an echocardiographic procedure. The introducer assembly includes an outer sheath having a tapered distal end and a passageway extending therethrough for passing the large instrument therethrough. The assembly further includes a dilator extending from the tapered distal end of the outer sheath for atraumatically dilating the esophagus during introduction. The assembly further includes an introducer guide for initial oral introduction into the esophagus and stomach of the patient. The outer sheath and dilator are interconnected at the proximal ends thereof for extending the tapered distal end of the dilator from the tapered distal end of the outer sheath. The interconnected outer sheath and dilator are then introduced atraumatically into the esophagus over the introducer guide. When positioned in the esophagus, the dilator is disconnected from the outer sheath, and the dilator and introducer guide are removed from the outer sheath and patient. A relatively large diagnostic instrument is introduced through the outer sheath for performing various diagnostic or treatment procedures. The inner and outer sheaths are comprised of a flexible material, with the outer diameter of the inner sheath being substantially less than the inner diameter of the outer sheath to maintain flexibility of the assembly during introduction into the esophagus.

18 Claims, 4 Drawing Sheets

OROESOPHAGEAL, INSTRUMENT INTRODUCER ASSEMBLY AND METHOD OF USE

TECHNICAL FIELD

This invention relates generally to oral, instrument introducers and, in particular, to an oroesophageal, instrument introducer assembly and a method of introducing large instruments such as an echotransducer positioned on the distal tip of a steerable gastroscope shaft through the introducer assembly.

BACKGROUND OF THE INVENTION

A conventional echocardiographic study is performed on the chest of a patient using a hand-held high frequency or ultrasound transducer for achieving a non-invasive examination of cardiac structures, function, and flow patterns. In some cases, however, the transducer beam cannot adequately image a particular cardiac structure or area due to the thickness of a patient's chest wall, surgical dressings positioned on the patient's chest wall, or a medical condition such as a chronic lung problem (emphysema).

A solution to these limitations in echocardiographic study is the transesophageal technique, which utilizes a miniaturized echotransducer positioned on the tip of a steerable gastroscope shaft. This transducer is introduced into the esophagus through the mouth, and the echocardiographic study is performed through the esophageal wall or stomach by directing the transducer beam toward the heart. A transesophageal echotransducer, which is commonly 14 by 13 mm in rectangular cross-sectional dimension, is traditionally positioned on the distal end of a gastroscope and inserted into the esophagus adjacent the heart. The transducer is moved and repositioned for attaining various images. In addition, a transducer is often removed and replaced with a different transducer for imaging a different angle, particularly since small bi-plane transducers are not commercially available.

A problem with the introduction and positioning of a transducer in the esophagus of a patient is that transducer movement causes gagging and considerable discomfort to conscious patients. As a result, sedation or even general anesthesia is used. Furthermore, transducer movement causes trauma to the esophagus as well as other complications such as aspiration, respiratory depression, esophageal perforation, and bleeding. Several anatomical structures, such as a sphincter, the lateral piriform recesses near the cricopharyngeal region, and the right angle arrangement between the mouth floor and the esophagus in the pharynx, present problematic areas for the physician to negotiate during the introduction, positioning, and exchange of a transducer.

A possible approach to minimizing these negative effects is to introduce a transducer through an endotracheal tube, which is conventionally used for establishing or maintaining an airway in a patient with respiratory problems. A limitation of endotracheal tubes is that they are used for providing an airway lumen. As a result, endotracheal tubes typically have a relatively small inside diameter and are formed of relatively stiff and unkinkable material. Therefore, endotracheal tubes are unsuitable for protecting the esophageal wall during introduction, positioning, and exchange of one or more transducers therethrough.

SUMMARY OF THE INVENTION

The foregoing problems are solved and a technical advance is achieved in an illustrative oroesophageal introducer assembly for introducing therethrough large instruments such as an echotransducer positioned on the distal tip of a steerable gastroscope for performing an echocardiographic procedure. The introducer assembly comprises an outer sheath having an atraumatic tapered distal end and a passage extending longitudinally therethrough that is sized for passing a large instrument such as the echotransducer and gastroscope therethrough. Advantageously, the size of the outer sheath passage is significantly larger than the passage of an endotracheal or nasopharyngeal tube to pass the diagnostic instrument therethrough. The tapered distal end of the outer sheath advantageously minimizes trauma during introduction of the sheath into the esophagus. To further advantageously minimize trauma to the esophagus during introduction, the introducer assembly includes a dilator positioned in the passage and extending from the tapered distal end of the outer sheath. The tapered distal end of the dilator has an outermost cross-sectional shape approximating that of the passage of the outer sheath to minimize any space therebetween and further minimize trauma to the esophagus during introduction of the assembly.

The introducer assembly further includes a guide tube having a closed, atraumatic distal end for oral insertion into the stomach of the patient by way of the esophagus. The introduced guide tube has a cross-sectional shape significantly less than that of the outer sheath to facilitate easy insertion into the esophagus and to atraumatically introduce the outer sheath thereover into the esophagus. The dilator also includes a passageway extending longitudinally therethrough approximating the cross-sectional shape of the guide tube to again minimize any space therebetween and further minimize trauma to the esophagus during introduction of the assembly into the esophagus of the patient. The guide tube further includes a plurality of side ports positioned proximate the closed, atraumatic distal end thereof to permit the attending physician to introduce air into the stomach using a syringe and confirm proper placement of the guide tube by auscultating over the stomach area. The guide tube further includes a removable connector fitting positioned in the passage of the guide tube proximate the proximal end thereof for connection to a syringe and introduction of air into the patient's stomach. The guide tube also includes a visible marker positioned on the outer surface of the tube a specified distance from the closed, atraumatic distal end thereof to further aid proper positioning of the guide tube into patient's stomach.

The dilator includes a distal tip piece of a semirigid material forming the tapered distal end of the dilator for advantageously dilating the esophagus during introduction therein. The dilator also includes an inner sheath of flexible material and a detachable connector fitting positioned in the passage proximate the proximal end of the inner sheath. The inner sheath has an outermost cross-sectional dimension substantially smaller than the innermost dimension of the cross-sectional shape of the outer sheath passage for advantageously maintaining the flexibility of the introducer assembly during oral introduction through the airway and into the esophagus. The introducer assembly also includes a mouthpiece positioned in the passage proximate the proximal end of the outer sheath. The mouthpiece includes a passage communicating with the passage of the outer sheath, which is sized for passing the large specified instrument therethrough. The dilator is positioned through the mouthpiece and outer sheath passage and fixed relative thereto when the mouthpiece and detachable connector fitting are interconnected. As a result, the tapered distal ends of the outer sheath and dilator present a smooth distal end for dilation of and insertion into the esophagus over the introducer guide. When introduced into the esophagus of the patient, the detachable connector fitting and mouthpiece are disconnected, and the inner dilator and guide tube are removed from the outer sheath and patient. A relatively large instrument such as an echotransducer positioned on the distal end of a gastroscope is then easily introduced atraumatically into the esophagus of the patient through the outer sheath of the introducer assembly.

The method of orally introducing the relatively large instrument into the esophagus of the patient includes inserting the introducer guide through the passage of the outer sheath and orally inserting the closed, atraumatic distal end of the introducer guide into the esophagus of the patient. The outer sheath and dilator are then orally introduced over the introducer guide into the esophagus of the patient. During the introduction procedure, the outer sheath and dilator are interconnected with the aid of a respective mouthpiece and connector fitting positioned at the proximal ends thereof. When the outer sheath is positioned in the esophagus of the patient, the dilator and introducer guide are removed from the outer sheath and patient. A relatively large instrument is then introduced through the outer sheath and into the patient.

DETAILED DESCRIPTION

Figure 1:
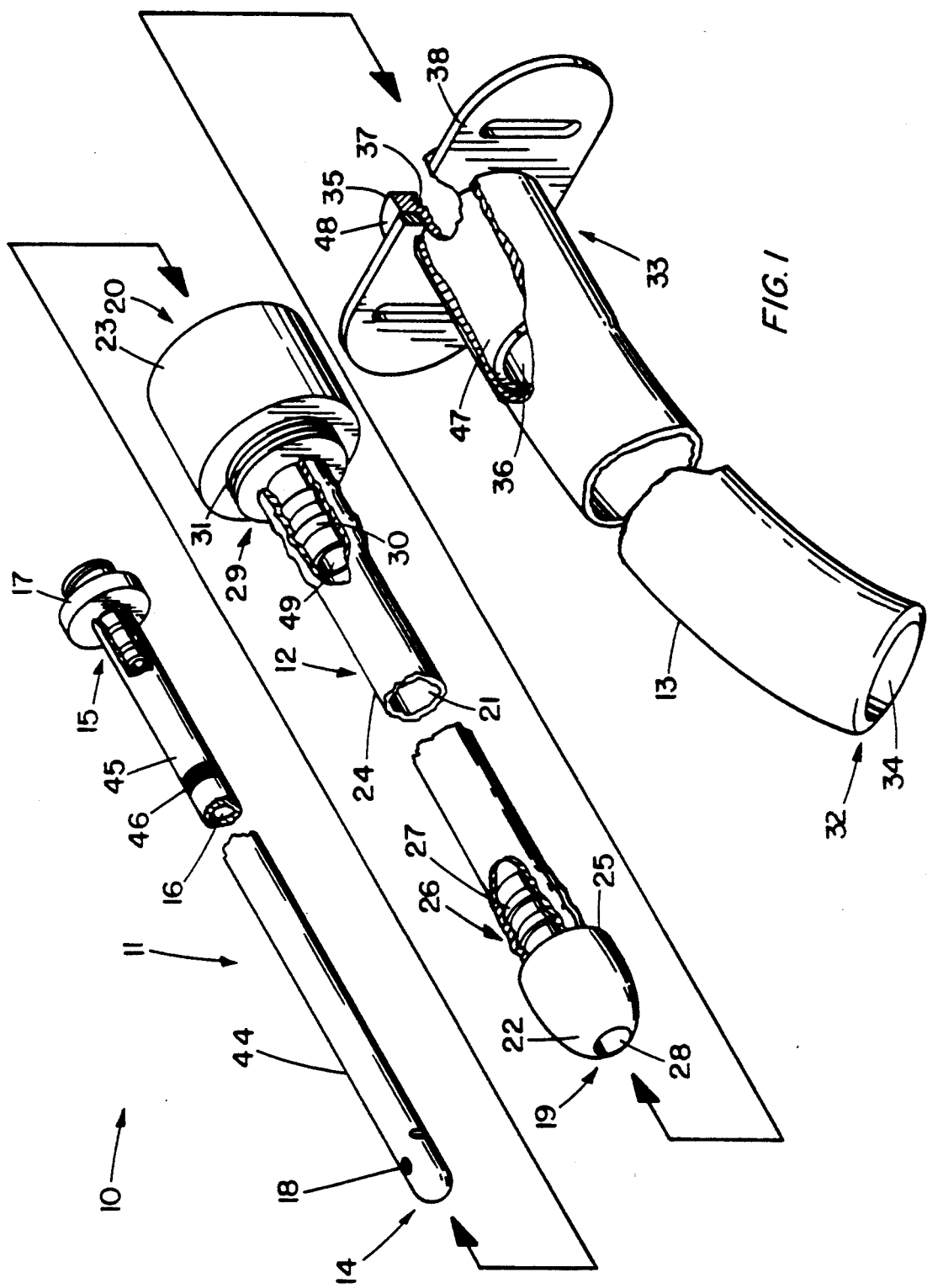
FIG. 1 depicts a partially sectioned pictorial view of an illustrative oroesophageal introducer assembly of the present invention for introducing a relatively large instrument into the esophagus of a patient.

FIG. 1 depicts a partially sectioned pictorial view of an illustrative oroesophageal introducer assembly 10 for introducing a relatively large instrument such as a transesophageal echotransducer into the esophagus of a patient and performing, for example, an echocardiographic procedure. Oroesophageal introducer assembly 10 comprises coaxial introducer guide 11, dilator 12, and outer sheath 13. The introducer guide includes a tube with a small outside diameter for extending from outside the mouth of a patient to the patient's stomach. The introducer guide provides for the introduction of the threadably interconnected dilator and outer sheath thereover and into the esophagus of the patient. When threadably interconnected, the tapered or bullet-shaped distal end of the dilator extends from the tapered distal end of the outer sheath to provide for the mechanical dilation of the esophagus and the atraumatic advancement of the outer sheath past problematic anatomical structures. After the outer sheath is desirably positioned in the esophagus, the introducer guide and dilator are disconnected, and the dilator and guide are removed from the outer sheath and patient. A transesophageal echotransducer is then atraumatically introduced through the outer sheath and positioned in the esophagus adjacent the heart of the patient.

Outer sheath 13 comprises a flexible material tube with tapered distal end 32, proximal end 33, and passage 34 extending longitudinally therethrough with, for example, a circular cross-sectional shape suitable for passing a relatively large instrument such as a transesophageal echotransducer therethrough. Mouthpiece 35 is positioned in passage 34 proximate the proximal end of the outer tubular sheath. When positioned in the esophagus, the patient bites on the distal portion of mouthpiece 35 and the proximal end of outer sheath 13. Flexible material outer tube 13 comprises, for example, a medical grade TYGON TM material and is approximately 23 cm in length with a 0.6875" outside diameter and a 0.5625" inside diameter. TYGON material is a vinyl blend material commercially available from Norton Industrial Plastics, Akron, Ohio. Tube 13 also includes a preformed longitudinal curvature with a gentle radius extending over the length thereof for enhancing the conformance of the outer sheath to the curvature of the mouth, throat, and esophagus of the patient.

Mouthpiece 35 comprises, for example, commercially available, semi-rigid DELRIN TM material and includes a distal tubular portion 47 with a proximal lip 48 extending radially therefrom. The distal tubular portion of the mouthpiece is positioned in passage 34 of tube 13. The distal mouthpiece portion includes passage 36 that extends longitudinally therethrough and forms the proximal end of outer sheath passage 34 for passing the relatively large instrument therethrough. The mouthpiece is approximately 4.3 cm in length with a 0.5625" inside diameter. Distal portion 47 is approximately 3.8 cm in length with a 0.6875" outside diameter. Mouthpiece lip 48 is 0.5 cm high with a 2.54 cm outside diameter. Mouthpiece 35 includes plurality 37 of internal threads positioned in passage 36 proximate the proximal end thereof for threadable interconnection with plurality 31 of external threads on the dilator. Mouthpiece 35 also includes flexible material flange 38 approximately 2.54 cm wide, 5.85 cm long, and with a central opening of 0.6875" for attaching a strap thereto, which is positioned around the patient's head and neck.

Dilator 12 includes tapered distal end 19, proximal end 20, and passage 21 extending longitudinally therethrough with, for example, a circular cross-sectional shape suitable for passing introducer guide 11 therethrough. Dilator 12 comprises inner tubular sheath 24, tapered or bullet-shaped distal tip piece 25, and detachable connector fitting 23, which are positioned in passage 21 of the inner tubular sheath proximate the distal and proximal ends, respectively. Tapered or bullet-shaped outer surface 22 of distal tip piece 25 forms tapered distal end 19 of the dilator and has an outermost cross-sectional shape, which is proximate the cross-sectional shape of passage 34 of outer tubular sheath 13 and longitudinally decreases in size from the cross-sectional shape of passage 34 to the cross-sectional shape of dilator passage 21. Detachable connector fitting 23 threadably interconnects with outer sheath 13, which fixes the relative longitudinal position of the dilator with respect to the outer sheath.

Tapered or bullet-shaped distal tip piece 25 comprises, for example, a commercially available semi-rigid DELRIN ™ material and is approximately 0.005" to 0.010" smaller in maximum outside diameter than the inside diameter (0.5625") of the outer sheath. The distal tip piece is inserted through passage 34 and extends distally from tapered distal end 32 of the outer sheath when the dilator and outer tubular sheath are threadably interconnected. Distal tip piece 25 includes proximal portion 26 with external barbs 27 for fixedly positioning the proximal end of the tip piece in the passage of the inner tubular sheath. The distal tip piece is approximately 1.5 cm in length and with a maximum outside diameter of 0.5625". The distal tip piece also further includes passage 28, which forms passage 21 about the distal end of the dilator.

Inner tubular sheath 24 comprises, for example, a flexible, medical grade TYGON material tube 44 approximately 23.5 cm in length with a 0.375" outside diameter and a 0.250" inside diameter with tapered or bullet-shaped distal tip piece 25 positioned partially in and extending from the distal end thereof. The outermost cross-sectional dimension or outside diameter of the inner tubular sheath is substantially less than the innermost dimension or inside diameter of dilator passage 34 of the outer tubular sheath for maintaining the overall flexibility of the introducer assembly during introduction.

Detachable connector fitting 23 comprises, for example, a well-known knurled knob including distal portion 29 with external barbs 30 for retaining the distal portion of the detachable connector fitting in the inner tube and with plurality 31 of external threads positioned proximal the ridges for interconnecting the dilator with the mouthpiece. The connector is approximately 1.5" long with a 0.250" inside diameter. Knurled knob is 1.9 cm high with a 2.39 cm outside diameter. Detachable connector fitting 23 includes a central passage 49, which forms the proximal end of the dilator passage 21.

Introducer guide 11 includes tube 44 with closed, atraumatic distal end 14, proximal end 15, and passage 16 extending longitudinally therein. Introducer guide 11 also includes a well-known Luer lock removable connector 17, which is positioned in passage 16 proximate proximal end 15 for attachment to a syringe, and side ports 18, which are positioned about the closed, atraumatic distal end for injection of air through passage 16. Introducer guide tube 44 comprises, for example, a commercially available, polyether urethane material and is approximately 95 cm in length with a 0.210" outside diameter (16 French) and a 0.142" inside diameter. The cross-sectional shape, particularly, the outside diameter, of the guide tube proximates the cross-sectional shape, particularly the inside diameter, of passage 21 of the dilator. This minimizes any gap therebetween and also minimizes trauma to the esophagus during introduction of the outer sheath and dilator. Introducer guide tube 44 has outer surface 45 with visible marker 46 positioned thereon a specified distance such as approximately 63.5 cm from closed distal end 14. Removable connector 17 comprises, for example, a well-known, barbed, female Luer lock connector.

Figure 2:
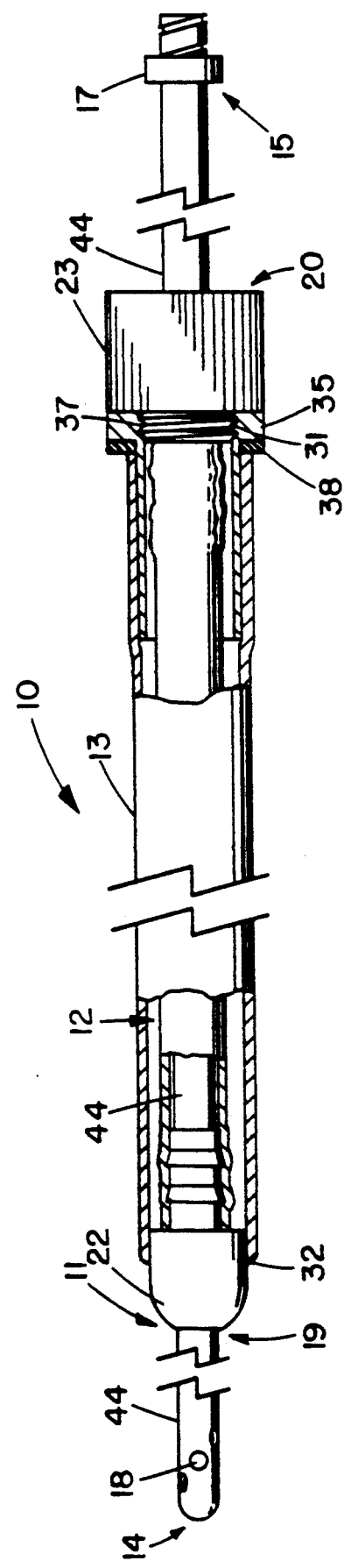
FIG. 2 depicts a longitudinal, partially sectioned view of the assembly of FIG. 1 coaxially positioned.

FIG. 2 depicts a longitudinal, partially sectioned view of oroesophageal introducer assembly 10 with previously described introducer guide 11, dilator 12, and outer sheath 13 coaxially positioned in preparation for introduction into the esophagus of a patient. When coaxially positioned, bullet-shaped outer surface 22 of tapered distal end 19 of the dilator extends from the tapered distal end 32 of outer sheath 13 for presenting an atraumatic dilatational surface to tissue. Closed, atraumatic distal end 14 of introducer guide 11 extends from the distal end of the dilator for insertion through the esophagus and into the stomach of the patient. Detachable connector fitting 23 of the dilator and mouthpiece 35 of the outer sheath are threadably interconnected with respective external threads 31 and internal threads 37 for fixing the relative position of the dilator and outer sheath during introduction.

Figure 3:
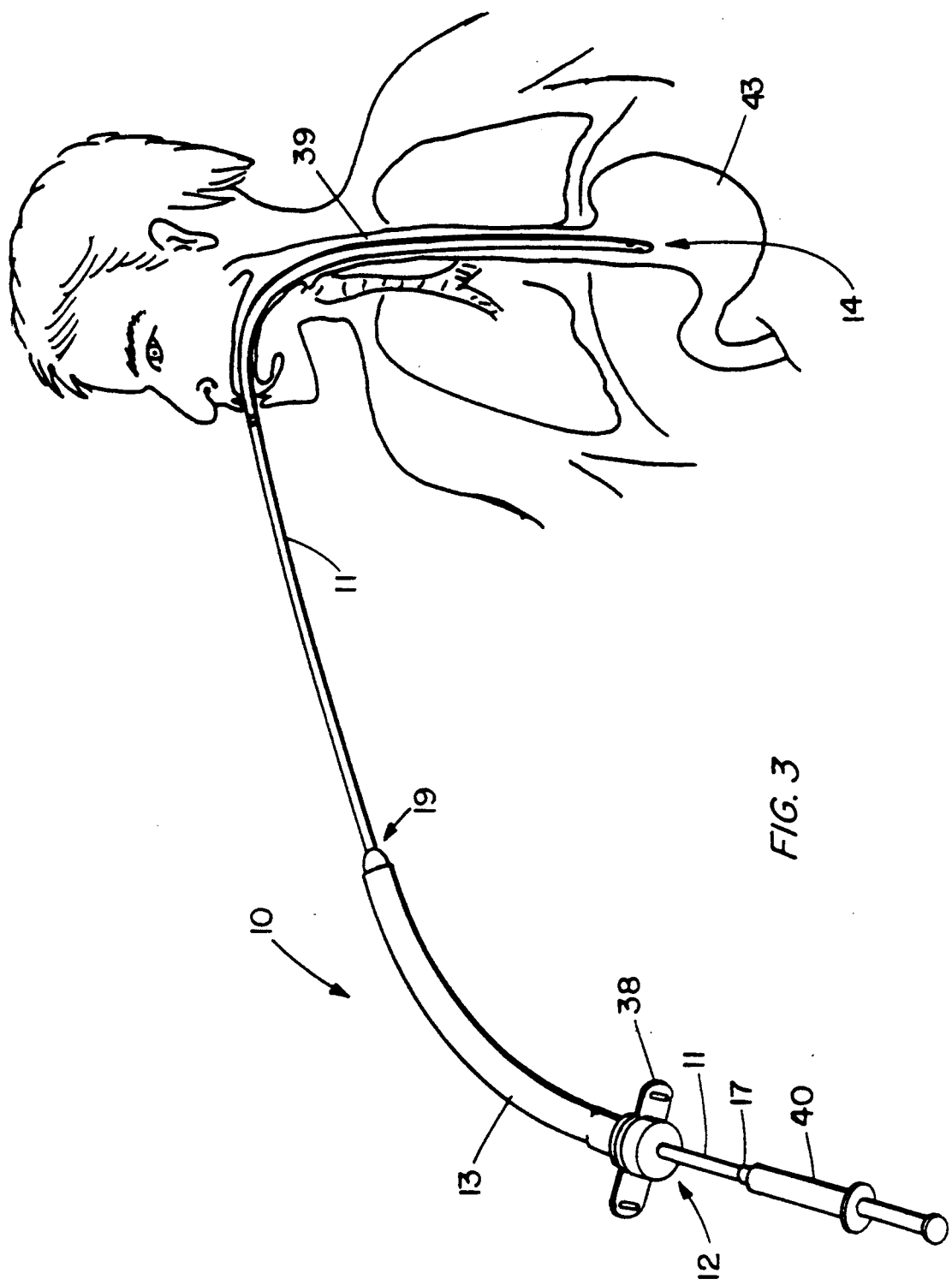
FIG. 3 depicts a longitudinal view of the assembly of FIG. 1 positioned in the esophagus of a patient.

FIG. 3 depicts a partially sectioned pictorial view of oroesophageal introducer assembly 10 including introducer guide 11 positioned through esophagus 39 of a patient with closed, atraumatic distal end 14 positioned in the patient's stomach 43. Syringe 40 is attached to the female luer lock connector 17 of the introducer guide for the injection of air for ascertaining placement in the stomach. The threadably interconnected outer sheath 13 and dilator 12 with tapered or bullet-shaped distal end 19 are positioned over the introducer guide and follow the introducer guide during introduction into the esophagus past problematic anatomical structures, such as the right angle arrangement between the mouth floor and the esophagus in the pharynx, and the lateral piriform recesses near the cricopharyngeal region. When the outer sheath is fully positioned in the esophagus of the patient, a strap is fastened through flange 38 of the outer sheath mouthpiece and about the head of the patient for stabilizing the position of the outer sheath. The detachable, dilator connector fitting is then unthreaded from the outer sheath mouthpiece, and the dilator and introducer guide are removed from the body of the patient.

Figure 4:
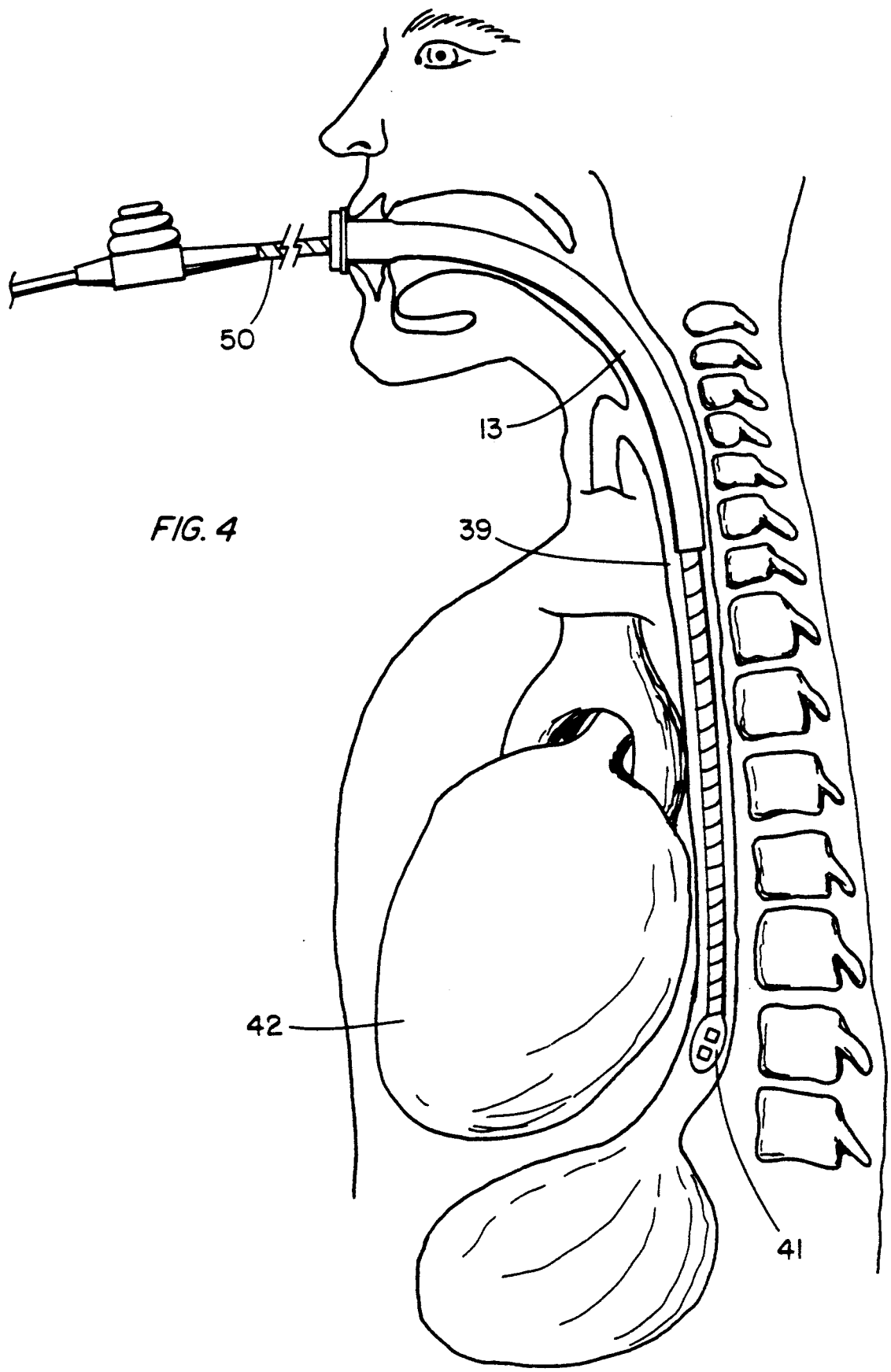
FIG. 4 depicts a longitudinal view of the outer sheath of FIG. 4 with a transesophageal echotransducer positioned therethrough and extending distally therefrom for imaging the heart of the patient.

FIG. 4 depicts a partially sectioned view of outer sheath 13 desirably positioned in esophagus 39 of the patient with gastroscope 50 and transesophageal echotransducer 41 positioned therethrough and extending distally therefrom for imaging heart 42. With outer sheath 13 in place, transesophageal echotransducer 41 positioned on the distal end of the gastroscope can be conveniently exchanged for another echotransducer while minimizing trauma to the esophagus and other anatomical structures.

It is to be understood that the above-described oroesophageal introducer assembly for introducing a transesophageal echotransducer is merely an illustrative embodiment of the principles of this invention and that other oroesophageal introducer assemblies may be devised by those skilled in the art without departing from the spirit and scope of this invention. For example, it is contemplated that the dilator, introducer guide, and outer sheath can be fabricated using flexible materials other than TYGON material or polyether urethane. Furthermore, it is contemplated that the distal tip piece can be fabricated using semi-rigid materials other than DELRIN material. It is also contemplated that the dilator and outer sheath be used without the aid of a introducer guide. It is also further contemplated that the introducer guide fitting, dilator connector fitting, and outer sheath mouthpiece be formed of other well-known or commercially available hub or connector fittings. It is also yet further contemplated that the distal end of the dilator have an outer surface that is tapered or beveled to result in a shape other than that resembling a bullet. It is still yet further contemplated that the outer sheath and dilator passages have varying cross-sectional shapes such as oval, elliptical, or any other shape to accommodate the introduction of any instrument therethrough and still maintain the overall flexibility of the outer sheath and dilator during introduction. The length of the assembly, particularly the outer sheath, can be varied for use with a gastroscope to examine the stomach or other parts of the gastrointestinal system. It is still yet further contemplated that the outer sheath can be used to retrieve foreign bodies from the stomach or to ligate varices in the esophagus. The size of the assembly, particularly the outer sheath, can be varied to adapt to the size of the patient such as with a child or with the various sizes of transducers.

What is claimed is:

1. An oroesophageal, instrument introducer assembly comprising:
    an outer sheath having a first tapered distal end, a proximal end, and a first passage extending longitudinally therethrough and including a first cross-sectional shape sized for passing a large specified instrument therethrough;
    a mouthpiece proximate said proximal end of said outer sheath and including a third passage communicating with said first passage of said outer sheath and sized for passing the large specified instrument therethrough; and
    a dilator having a proximal end, a second tapered distal end extending from said first tapered distal end of said outer sheath when positioned in said first passage of said outer sheath, and a second passage extending longitudinally therethrough and including a second cross-sectional shape smaller than said first cross-sectional shape of said first passage, said second tapered distal end having an outermost cross-sectional shape proximate said first cross-sectional shape of said first passage and longitudinally decreasing in size from said first cross-sectional shape of said first passage to said second cross-sectional shape of said second passage.

2. The introducer assembly of claim 1 further comprising an introducer guide having a third cross-sectional shape proximate said second cross-sectional shape of said second passage of said dilator.

3. The introducer assembly of claim 2 wherein said introducer guide includes a tube having a closed, atraumatic distal end, a proximal end, a third passage extending longitudinally therein, and a plurality of side ports positioned proximate to said closed distal end and communicating with said third passage.

4. The introducer assembly of claim 3 wherein said introducer guide further includes a removable connector positioned in said third passage proximate said proximal end of said tube.

5. The introducer assembly of claim 3 wherein said introducer guide further includes a visible marker positioned on an outer surface of said tube a specified distance from said closed distal end.

6. The introducer assembly of claim 1 wherein said outer sheath comprises a flexible material tube.

7. The introducer assembly of claim 1 wherein said dilator includes a connector fitting positioned proximate a proximal end thereof and having a passage therein communicating with said second passage, said connector fitting being interconnectable with said mouthpiece.

8. The introducer assembly of claim 1 wherein said dilator includes an inner sheath.

9. The introducer assembly of claim 8 wherein said inner sheath comprises a flexible material tube.

10. The introducer assembly of claim 8 wherein said inner sheath has an outermost cross-sectional dimension substantially smaller than an innermost dimension of said first cross-sectional shape of said first passage.

11. The introducer assembly of claim 8 wherein said dilator further includes a distal tip piece including said second tapered distal end and positioned in a passage of said inner sheath proximate a distal end thereof.

12. The introducer assembly of claim 11 wherein said distal tip piece comprises a semi-rigid material.

13. The introducer assembly of claim 8 further comprising a detachable connector fitting positioned in said second passage of said inner sheath proximate said proximal end thereof, said connector fitting being insertable in said third passage of said mouthpiece and being interconnectable with said mouthpiece.

14. An oroesophageal, instrument introducer assembly comprising:
    an outer, flexible material tube having a first tapered distal end, a proximal end, and a first passage extending longitudinally therethrough, said first passage having a first cross-sectional shape sized for passing a large specified instrument therethrough;
    a mouthpiece positioned in said first passage proximate said proximal end of said outer tube and including a passage communicating with said first passage and sized for passing the large specified instrument therethrough;
    an inner, flexible material tube having a distal end, a proximal end, and a second passage extending longitudinally therethrough, said second passage having a second cross-sectional shape;
    a dilator piece positioned in said second passage and proximate said distal end of said inner tube and having a second tapered distal end extending from said first tapered distal end of said outer tube when said inner tube is positioned in said first passage of said outer tube and also having an outermost cross-sectional shape approximating said first cross-sectional shape of said first passage and longitudinally decreasing in size from said first cross-sectional shape of said first passage to said second cross-sectional shape of said second passage;
    a detachable connector positioned in said second passage and proximate said proximal end of said inner tube and interconnectable with said mouthpiece;
    a guide tube insertable through said detachable connector, said second passage of said inner tube, and said dilator and having a closed, atraumatic distal end, a proximal end, a passage extending therein, and a plurality of ports proximate said closed distal end and communicating with said passage thereof;
    a visible marker on an outer surface of said guide tube and positioned a specified distance from said closed distal end; and
    a removable connector positioned in said passage of said guide tube.

15. A method of orally and introducing a large specified instrument into an esophagus of a patient, comprising the steps of:
    providing an outer sheath having a first tapered distal end, a proximal end, and a first passage extending longitudinally therethrough and including a first cross-sectional shape sized for passing a large specified instrument therethrough;
    providing a dilator having a proximal end, a second tapered distal end extending from said first tapered distal end of said outer sheath when positioned in said first passage of said outer sheath, and a second passage extending longitudinally therethrough and including a second cross-sectional shape smaller than said first cross-sectional shape of said first passage, said second tapered distal end having an outermost cross-sectional shape proximate said first cross-sectional shape of said first passage and decreasing in size from said first cross-sectional shape of said first passage to said second cross-sectional shape of said second passage;

providing an introducer guide having a third cross-sectional shape proximate said second cross-sectional shape of said second passage of said dilator;

positioning said dilator in said first passage of said outer sheath with said second tapered distal end of said dilator extending from said first tapered distal end of said outer sheath;

inserting said introducer guide through said second passageway of said dilator;

orally inserting a distal end of said introducer guide through an esophagus and into a stomach of a patient;

orally introducing said outer sheath and said dilator over said introducer guide into the esophagus of the patient; and removing said dilator and said introducer guide from the patient when the outer sheath is positioned in the esophagus of the patient.

16. The method of claim 15 further comprising the step of introducing a large specified instrument through the outer sheath into the esophagus of the patient.

17. The method of claim 15 further comprising the steps of:

providing a mouthpiece positioned in said first passage proximate said proximal end of said outer sheath;

providing a connector fitting positioned in said second passage proximate said proximal end of said dilator; and interconnecting said mouthpiece and said connector fitting.

18. The method of claim 15 further comprising the step of providing said dilator with an inner sheath of a flexible material, said inner sheath having an outermost cross-sectional dimension substantially less than an outermost dimension of said first cross-sectional shape of said first passage of said outer sheath.

* * * * *